United States Patent
Liu et al.

(10) Patent No.: US 11,596,978 B2
(45) Date of Patent: *Mar. 7, 2023

(54) ELECTROSURGICAL ULTRASONIC VESSEL SEALING AND DISSECTING SYSTEM

(71) Applicant: COVIDIEN LP, Mansfield, MA (US)

(72) Inventors: Xiaosen Liu, College Station, TX (US); Adrian I. Colli-Menchi, College Station, TX (US); James A. Gilbert, Boulder, CO (US); Daniel A. Friedrichs, Aurora, CO (US); Keith W. Malang, Longmont, CO (US); Edgar Sanchez-Sinencio, College Station, TX (US)

(73) Assignee: COVIDIEN LP, Mansfield, MA (US)

( * ) Notice: Subject to any disclaimer, the term of this patent is extended or adjusted under 35 U.S.C. 154(b) by 1207 days.

This patent is subject to a terminal disclaimer.

(21) Appl. No.: 16/132,640

(22) Filed: Sep. 17, 2018

(65) Prior Publication Data

US 2019/0076675 A1   Mar. 14, 2019

Related U.S. Application Data

(63) Continuation of application No. 14/797,301, filed on Jul. 13, 2015, now Pat. No. 10,086,217.

(Continued)

(51) Int. Cl.
*B06B 1/02* (2006.01)
*A61B 17/32* (2006.01)
(Continued)

(52) U.S. Cl.
CPC .... *B06B 1/0261* (2013.01); *A61B 17/320068* (2013.01); *A61B 2017/0003* (2013.01);
(Continued)

(58) Field of Classification Search
CPC .............. B06B 1/0261; B06B 2201/76; A61B 17/320068; A61B 2017/0003;
(Continued)

(56) References Cited

U.S. PATENT DOCUMENTS

| 4,750,488 A | 6/1988 | Wuchinich |
| 4,750,902 A | 6/1988 | Wuchinich et al. |

(Continued)

FOREIGN PATENT DOCUMENTS

| JP | S63500850 A | 3/1988 |
| JP | 7181204 A | 7/1995 |

(Continued)

OTHER PUBLICATIONS

Notice of Allowance issued by the Japanese Patent Office in corresponding Japanese Patent Application No. 2016-196119 dated Aug. 14, 2019 with English translation.

(Continued)

*Primary Examiner* — Ronald Hupczey, Jr.
(74) *Attorney, Agent, or Firm* — Carter, DeLuca & Farrell LLP

(57) ABSTRACT

An ultrasonic motion generator includes a non-resonant inverter, an ultrasonic transducer, and a comparator. The non-resonant inverter inverts direct current (DC) to alternating current (AC) having a first frequency. The ultrasonic transducer is electrically coupled with the non-resonant inverter and generates an ultrasonic motion based on the inverted AC. The comparator automatically detects a deviation of the first frequency from a resonant frequency of the ultrasonic transducer based on motion current passing through the ultrasonic transducer and generates an output signal based on the deviation to drive the non-resonant inverter.

19 Claims, 10 Drawing Sheets

Related U.S. Application Data

(60) Provisional application No. 62/028,916, filed on Jul. 25, 2014.

(51) Int. Cl.
  *A61B 17/00* (2006.01)
  *A61N 7/00* (2006.01)
  *A61B 18/00* (2006.01)

(52) U.S. Cl.
  CPC ............... *A61B 2017/00106* (2013.01); *A61B 2017/320094* (2017.08); *A61B 2017/320095* (2017.08); *A61B 2018/00726* (2013.01); *A61B 2018/00827* (2013.01); *A61B 2018/00845* (2013.01); *A61N 7/00* (2013.01); *B06B 2201/76* (2013.01)

(58) Field of Classification Search
  CPC ......... A61B 2017/00106; A61B 2017/320094; A61B 2017/320095; A61N 7/00
  See application file for complete search history.

(56) References Cited

U.S. PATENT DOCUMENTS

| | | | |
|---|---|---|---|
| 5,406,503 | A | 4/1995 | Williams, Jr. et al. |
| 5,832,412 | A | 11/1998 | Guez |
| 5,866,968 | A | 2/1999 | Mech |
| 6,016,052 | A | 1/2000 | Vaughn |
| 6,469,418 | B1 | 10/2002 | Katerberg et al. |
| 8,258,886 | B2 | 9/2012 | Gilbert |
| 8,665,031 | B2 | 3/2014 | Gilbert |
| 10,086,217 | B2 * | 10/2018 | Liu ........................ B06B 1/0261 |
| 2005/0288659 | A1 | 12/2005 | Kimura et al. |
| 2011/0082486 | A1 | 4/2011 | Messerly et al. |
| 2011/0092886 | A1 | 4/2011 | Raney |
| 2011/0257650 | A1 | 10/2011 | Deville |
| 2013/0331874 | A1 | 12/2013 | Ross et al. |
| 2014/0132113 | A1 | 5/2014 | Grohmann |

FOREIGN PATENT DOCUMENTS

| | | |
|---|---|---|
| JP | 8117687 A | 5/1996 |
| JP | 2002514958 A | 5/2002 |
| JP | 5346441 B2 | 11/2013 |
| JP | 2013255798 A | 12/2013 |
| WO | 87/01276 A1 | 3/1987 |
| WO | 98/53508 A1 | 11/1998 |

OTHER PUBLICATIONS

Notice of Reasons for Rejection issued by the Japanese Patent Office dated May 9, 2019 in corresponding Japanese Patent Application No. 2016-196119 with English translation.
Australian Examination Report for corresponding AU Application No. 2015204334, dated Jan. 6, 2017, 3 pages.
English translation of Japanese Notice of Allowance in corresponding Application No. 2015-146694, dated Mar. 31, 2017, 2 pages.
Japanese Office Action issue in corresponding JP Application No. 2015-146694, dated Jul. 27, 2016.
European Extended Search Report in corresponding application No. EP 15 17 8067 dated Mar. 2, 2016.
European Examination Report dated Jan. 15, 2021 issued in corresponding EP Appln. No. 15178067.3.

* cited by examiner

ELECTROSURGICAL ULTRASONIC VESSEL SEALING AND DISSECTING SYSTEM

CROSS-REFERENCE TO RELATED APPLICATIONS

The present application is a continuation application of U.S. patent application Ser. No. 14/797,301, filed on Jul. 13, 2015, which claims the benefit of and priority to U.S. Provisional Application Ser. No. 62/028,916, filed on Jul. 25, 2014, the entire contents of all of the foregoing applications are incorporated herein by reference.

BACKGROUND

Technical Field

The present disclosure relates to an ultrasonic surgical system for treating tissue. More particularly, the present disclosure relates to an ultrasonic surgical system that automatically tracks the resonant frequency of the ultrasonic transducer of the ultrasonic surgical system.

Background of Related Art

Ultrasonic surgical devices have been demonstrated to provide outstanding hemostasis and efficient dissection of tissue with minimum lateral thermal damage and low smoke generation. Unlike electrosurgical devices, which require electrical current to flow through a patient, ultrasonic surgical devices operate by applying mechanical action of an ultrasonic transducer that is driven at a mechanical resonant frequency.

The Phase-lock-loop (PLL) technique has been used to generate ultrasonic mechanical motion having a resonant frequency by locking a phase in a reliable range so that the signals are prevented from becoming unstable. However, the PLL technique tends to be complex, and difficult to stabilize under large transient loading conditions. Further, the PLL technique needs more computational power to accurately lock the phases between a power source and outputs of the ultrasonic transducer, and thus necessarily includes a time lag which might cause harm to patients. As a result, simpler and less computationally complex ultrasonic surgical systems for treating tissue are desired.

SUMMARY

The present disclosure features ultrasonic surgical systems and ultrasonic motion generators, which include an ultrasonic transducer and automatically track the resonant frequency of the ultrasonic transducer.

In an embodiment, an ultrasonic motion generator includes a non-resonant inverter, an ultrasonic transducer, and a comparator. The non-resonant inverter inverts direct current (DC) to alternating current (AC) having a first frequency. The ultrasonic transducer is electrically coupled with the non-resonant inverter and generates an ultrasonic motion based on the inverted AC. The comparator automatically detects a deviation of the first frequency from a resonant frequency of the ultrasonic transducer based on motion current passing through the ultrasonic transducer and generates an output signal based on the deviation to drive the non-resonant inverter.

In an aspect, a longitudinal displacement of the ultrasonic motion is based on a load operably connected to the ultrasonic motion generator.

In an aspect, the ultrasonic transducer is modeled as a band-pass filter including a resistor, a capacitor, and an inductor connected in series. The resonant frequency of the ultrasonic transducer is defined by $$\frac{1}{\sqrt{L \cdot C}},$$

where L is an inductance of the inductor and C is a capacitance of the capacitor. In a frequency domain, a magnitude of a product of a gain of the comparator and a gain of the band-pass filter is substantially equal to one. Additionally, in the frequency domain, a phase of the product of the gain of the comparator and the gain of the band-pass filter is substantially equal to an integer multiple of two Pi radians.

In an aspect, the comparator has a high open loop gain.

In another aspect, the ultrasonic motion generator further includes a transformer electrically coupled with the non-resonant inverter and the ultrasonic transducer, and configured to control an amplitude of the AC inverted by the non-resonant inverter.

In another aspect, the non-resonant inverter is controlled by a digital resonant signal based on the output signals of the comparator.

In another embodiment, an ultrasonic apparatus for treating tissue includes a power source configured to output direct current, an ultrasonic motion generator, a sensor, and a controller. The ultrasonic motion generator includes a non-resonant inverter, an ultrasonic transducer, and a comparator. The non-resonant inverter inverts DC to AC having a first frequency. The ultrasonic transducer is electrically coupled with the non-resonant inverter and generates an ultrasonic motion based on the inverted AC. The comparator automatically detects a deviation of the first frequency from a resonant frequency of the ultrasonic transducer based on motion current passing through the ultrasonic transducer and generates an output signal based on the deviation to drive the non-resonant inverter. The sensor senses the DC passing from the power source to the ultrasonic motion generator. The controller is coupled with the sensor and the comparator and controls the amplitude of the DC.

In an aspect, a longitudinal displacement of the ultrasonic motion is based on a load operably connected to the ultrasonic motion generator.

In an aspect, the ultrasonic transducer is modeled as a band-pass filter including a resistor, a capacitor, and an inductor connected in series. The resonant frequency of the ultrasonic transducer is defined by $$\frac{1}{\sqrt{L \cdot C}},$$

where L is an inductance of the inductor and C is a capacitance of the capacitor. In a frequency domain, a magnitude of a product of a gain of the comparator and a gain of the band pass filter is substantially equal to one. Additionally, in the frequency domain, a phase of the product of the gain of the comparator and the gain of the band pass filter is substantially equal to an integer multiple of two Pi radians.

In an aspect, the comparator has a high open loop gain.

In another aspect, the power source includes a power supply configured to generate the DC power and a converter configured to modulate the DC power.

In another aspect, the controller generates a digital pulse-width modulation signal based on the sensed DC to drive the converter.

In yet another aspect, the controller further generates a digital resonant signal based on the output signal to drive the non-resonant inverter.

In another aspect, the ultrasonic motion generator further includes a transformer electrically coupled with the non-resonant inverter and the ultrasonic transducer, and the transformer controls an amplitude of the AC inverted by the non-resonant inverter.

In yet another aspect, a longitudinal displacement of the ultrasonic motion is based on an amplitude of the DC converted by the converter In yet another embodiment, an ultrasonic system for treating tissue includes an ultrasonic surgical apparatus and an end effector. The ultrasonic surgical apparatus includes a power source configured to output direct current, an ultrasonic motion generator, a sensor, and a controller. The ultrasonic motion generator includes a non-resonant inverter, an ultrasonic transducer, and a comparator. The non-resonant inverter inverts DC to AC having a first frequency. The ultrasonic transducer is electrically coupled with the non-resonant inverter and generates an ultrasonic motion based on the inverted AC. The comparator automatically detects a deviation of the first frequency from a resonant frequency of the ultrasonic transducer based on motion current passing through the ultrasonic transducer and generates an output signal based on the deviation to drive the non-resonant inverter. The sensor senses the DC passing from the power source to the ultrasonic motion generator. The controller is coupled with the sensor and the comparator and controls the amplitude of the DC. The end effector applies the generated ultrasonic motion to tissue for sealing or dissecting the tissue.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1A:
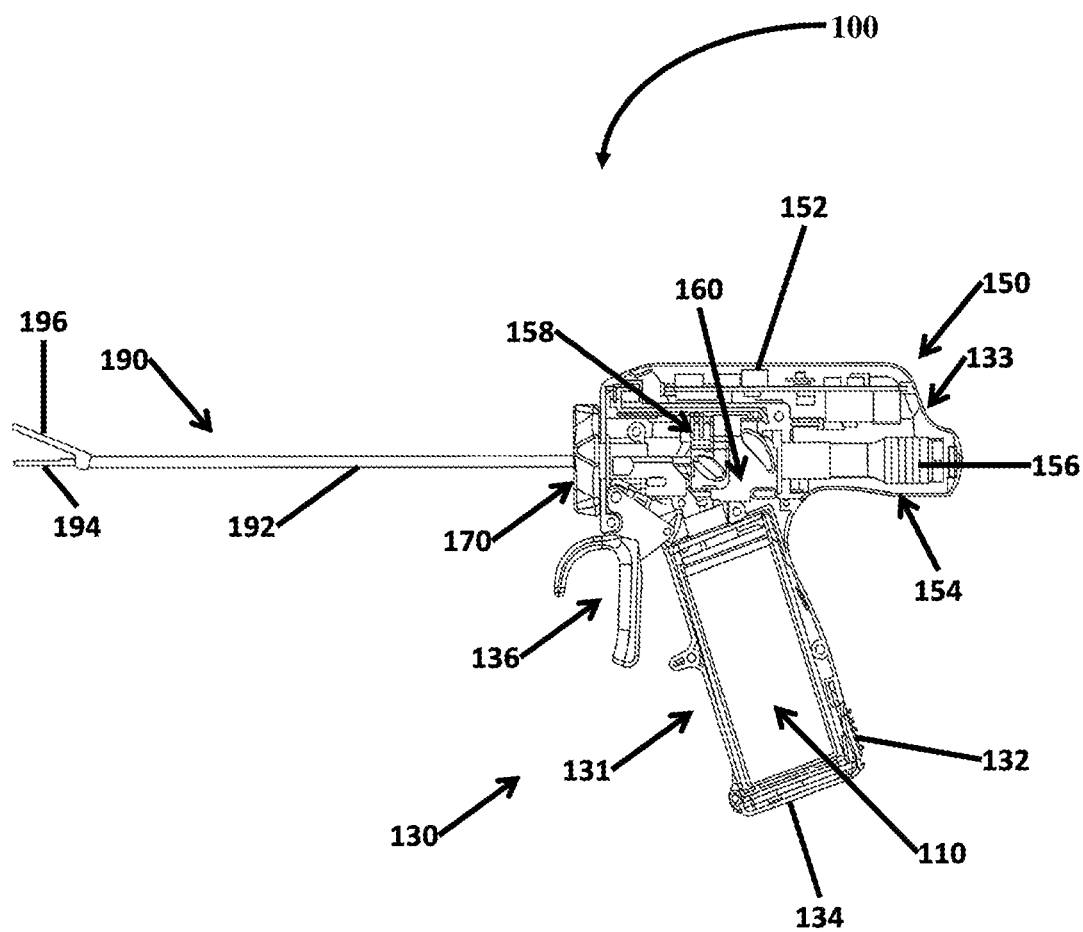
FIG. 1A is a side elevation view of an ultrasonic surgical system in accordance with embodiments of the present disclosure.

Generally, the present disclosure provides an ultrasonic surgical system for treating, e.g., sealing and dissecting, tissue. The ultrasonic surgical system utilizes an ultrasonic mechanical motion generator that follows an electronic circuit model for automatically tracking the resonant frequency. In particular, the ultrasonic surgical system automatically tracks its resonant frequency without requiring any computational operations to be performed by a processor. The ultrasonic surgical system includes an ultrasonic transducer, which is based on a band-pass filter oscillator architecture. Tissue treatment is achieved by the mechanical action of the ultrasonic transducer that is driven at the proper mechanical resonant frequency by a comparator.

A pulse-width modulation (PWM) amplitude control is employed to regulate the mechanical motion of an end effector and to provide different levels of power for treating tissue. Further, a proportional-integral (PI) controller is included to obtain a rapid transient response to changes in load and to maintain stable surgical operations.

The ultrasonic surgical system includes two control loops to control the mechanical ultrasonic motion of the ultrasonic transducer. The first loop is an amplitude control loop to control the average power delivered to the ultrasonic transducer to regulate the longitudinal mode displacement and includes a closed-loop feedback control. The amplitude of the DC power is proportional to the amount of longitudinal mode displacement of the ultrasonic transducer. The second loop generates an AC signal from the DC input and automatically tracks the resonant frequency of the ultrasonic transducer, which is based on a band-pass filter oscillator. By using the first and second control loops, the ultrasonic surgical system provides regulated mechanical ultrasonic motion at resonant frequency sufficient to treat tissue in accordance with embodiments of this disclosure.

Referring now to the drawing figures, the presently disclosed ultrasonic surgical system will be described in detail, beginning initially with FIGS. 1A-1B, which illustrate an ultrasonic surgical system 100 for treating tissue. The ultrasonic surgical system 100 includes a power source 110, a housing 130, an ultrasonic transducer 150, and an end effector 190. The power source 110 provides DC power to the ultrasonic transducer 150. In an aspect, the power source 110 may be a battery that directly provides DC power. In a further aspect, the power source 110 may be insertable or incorporated into the housing 130 so that the ultrasonic surgical system 100 may be portably carried without disturbances of any cable. In yet another aspect, the power source 110 may be rechargeable so that the power source 110 may be reusable for a certain amount of time.

In another aspect, the power source 110 may be connected to an alternating current (AC) power source and invert the AC power to DC power. The AC power source may be of a relatively low frequency, such as 60 hertz (Hz), while the ultrasonic surgical system 100 needs a higher frequency power, such as 55.5 kilo hertz (kHz). Thus, the power source 110 may convert the low frequency AC power to DC power so that the DC power may be inverted to AC power having a frequency suitable to cause the ultrasonic transducer 150 to generate mechanical ultrasonic motion.

Figure 1B:
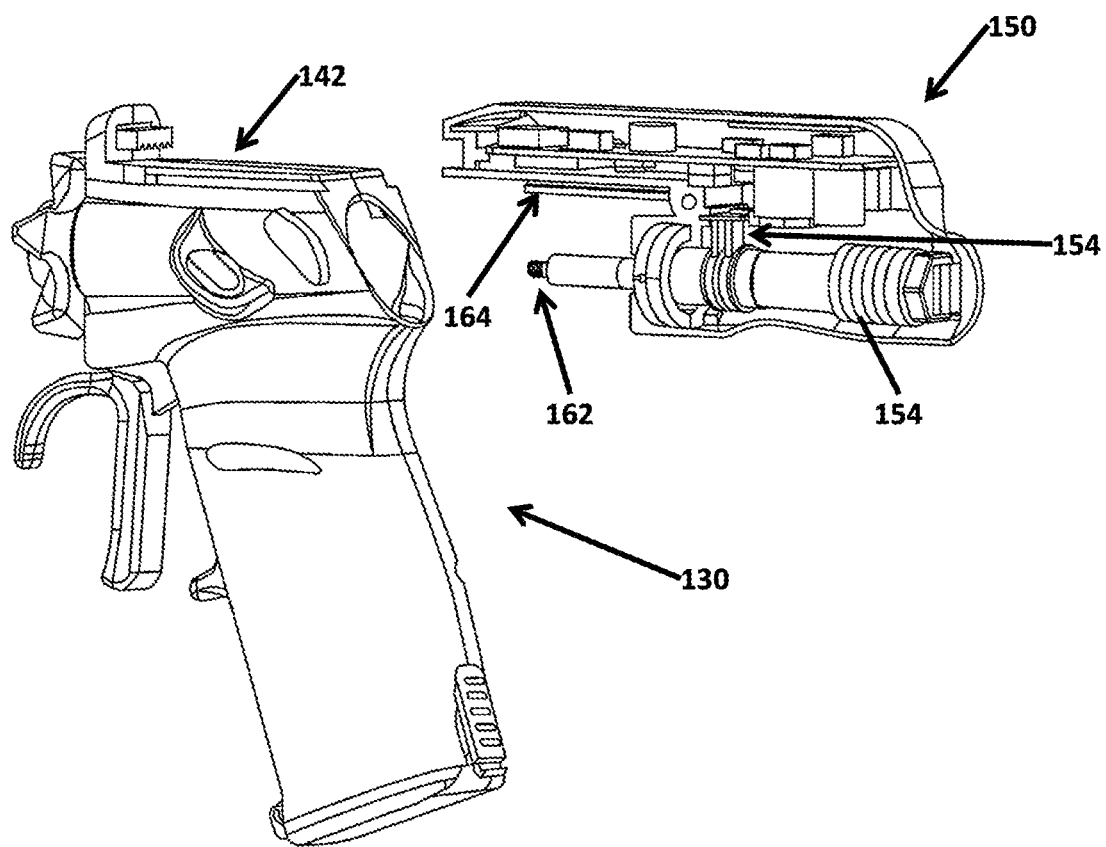
FIG. 1B is a perspective cutaway view of a handle and an ultrasonic transducer of the ultrasonic surgical system of FIG. 1A in accordance with embodiments of the present disclosure.

With continued reference to FIGS. 1A and 1B, the housing 130 includes a handle portion 131 and a cover 133. The handle portion 131 includes a compartment 132 which houses the power source 110 when the power source 110 is inserted, and a power source door 134 that allows the power source 110 to be inserted into the compartment 132 when opened. In an aspect, the power source door 134 may create a water-tight seal between the interior and the exterior of the compartment 132. The handle portion 131 further includes a trigger 136. When the trigger 136 is squeezed, the power source 110 is electrically connected to the ultrasonic transducer 150 so that the ultrasonic transducer 150 is powered to generate mechanical ultrasonic motion. When the trigger 136 is released, the power source is electrically disconnected with the ultrasonic transducer 150.

The cover 133 provides protection by covering the ultrasonic transducer 150. The ultrasonic transducer 150 includes a generator assembly 152 and a transducer assembly 154. The generator assembly 152 is electrically connected with the transducer assembly 154 via a pair of contacts 158. The generator assembly 152 receives the DC power from the power source 110 and generates AC signals having an ultrasonic frequency. The generator 152 assembly may be capable of generating signals having a different frequency based on a surgical operation. For example, the generator assembly 152 generates AC signals having a frequency from about 40 kHz to about 60 kHz.

The transducer assembly 154 includes a transducer body 156 and a transducer attachment port 160. The transducer body 156 receives the AC signal generated by the generator assembly 152 and generates mechanical ultrasonic motion based on the amplitude and the frequency of the generated AC signal. The transducer body 156 includes piezoelectric material, which converts the generated AC signal to mechanical ultrasonic motion. The transducer body 156 may be based on an electrical oscillator model having an inductor and a capacitor, which oscillates between charging and discharging. This oscillation model for the transducer body 156 is described further in detail below.

The cover 133 also includes a spindle 170, which is formed with indentations so that a user can easily rotate the spindle 170. When spindle 170 is rotated clockwise, the end effector 190 is attached to the housing and is mechanically connected to the ultrasonic transducer 150 via the transducer attachment port 160 so that the end effector 190 conveys the mechanical ultrasonic motion to treat tissue. In an aspect, the spindle 170 may rotate the end effector 190 so that the end effector 190 may provide sealing and/or dissecting tissue in any proper angle.

The end effector 190 includes waveguides 192 and 194, and a jaw member 196. The end effector 190 is mechanically connected with the transducer body 156 via the transducer attachment port 160. When the trigger 136 is activated, e.g. it is squeezed or pulled, the pair of contacts 158 makes an electrical connection between the generator assembly 152 and the transducer body 156, such that the signals generated by the generator assembly 152 cause the transducer body 156 to physically vibrate longitudinally and thereby generate mechanical ultrasonic motion. In an aspect, the transducer attachment port 160 may have a locking portion around which the end effector 190 rotates to make a physical coupling with the transducer body 156. Through this physical coupling, the end effector 190 conveys the mechanical ultrasonic motion from the transducer body 156 to tissue via the waveguides 192 and 194.

The jaw member 196 also has a pivoting arm that acts to grasp or clamp onto tissue between the jaw member 196 and the waveguide 194. When the jaw member 196 and the waveguide 194 grasp tissue and only the waveguide 194 conveys the mechanical ultrasonic motion, temperature of the grasped tissue between the waveguide 194 and the jaw member 196 increases due to the mechanical motion. According to the amplitude and the frequency of the mechanical motion, the grasped tissue may be dissected or sealed.

FIG. 1B illustrates the ultrasonic transducer 150 separate from the handle portion 131 of the housing 130 of FIG. 1A. The pair of connectors 158 is connected to the round groove of the ultrasonic transducer 150 so that the rotational movement of the ultrasonic transducer 150 does not disrupt the connection between the ultrasonic transducer 150 and the generator assembly 152. Thus, the ultrasonic transducer 150 is able to freely rotate within the housing 130. The ultrasonic transducer 150 further includes an outer coupling 162 which physically and/or mechanically locks the end effector 190 to the ultrasonic transducer 150.

The ultrasonic transducer 150 includes a first connector 164 and the handle portion 131 of the housing 130 includes a second connector 142. The first connector 164 and the second connector 142 may be selectively removable from the ultrasonic transducer 150 and the handle portion 131, respectively.

Figure 2:
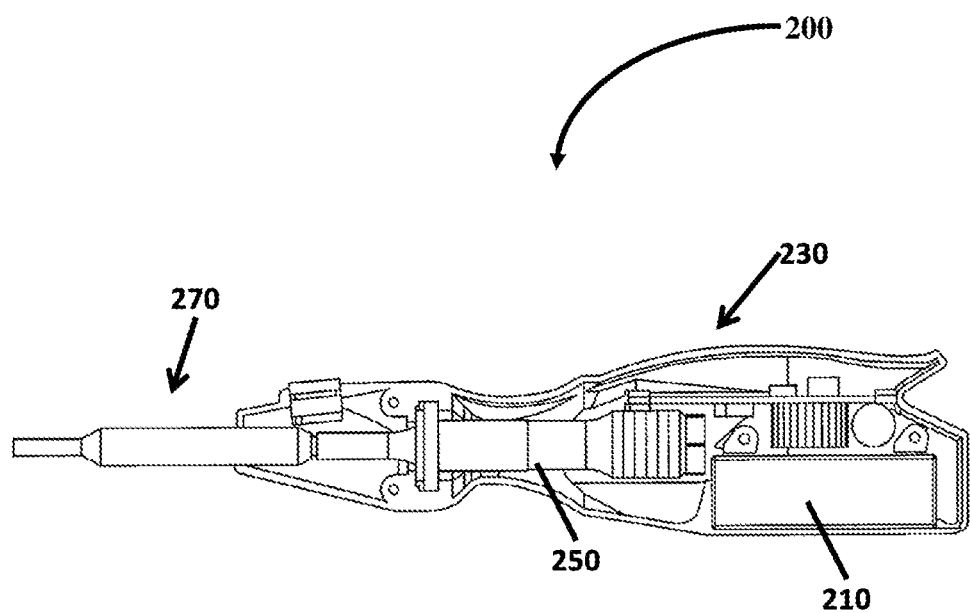
FIG. 2 is a side elevation view of an ultrasonic surgical pen system in accordance with embodiments of the present disclosure.

FIG. 2 shows an ultrasonic surgical pen device 200, which is another illustrative embodiment of the ultrasonic surgical system 100 of FIG. 1A. The ultrasonic surgical pen device 200 includes a power source 210, the housing 230, the ultrasonic transducer 250, and the end effector 290. Descriptions for the power source 210, the housing 230, the ultrasonic transducer 250, the end effector 290 are similar to those for the power source 110, the housing 130, the ultrasonic transducer 150, and the end effector 190 of FIG. 1A and are thus omitted.

Figure 3:
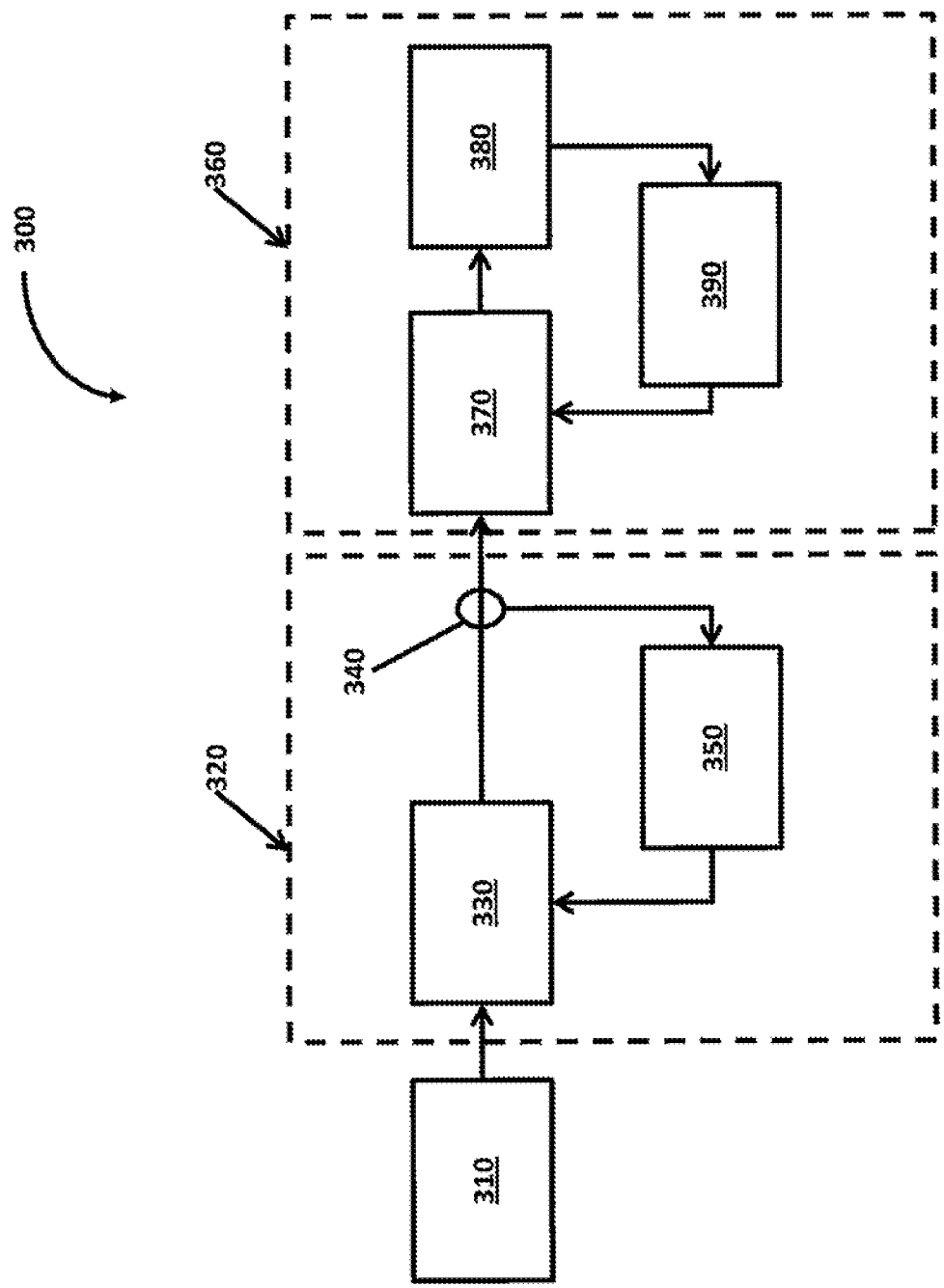
FIG. 3 is a block diagram of an ultrasonic surgical system in accordance with embodiments of the present disclosure.

FIG. 3 illustrates a ultrasonic surgical system 300, e.g., ultrasonic surgical system 100 or 200 of FIGS. 1A and 2, using a band-pass filter (BPF) oscillator architecture, which automatically tracks the resonant frequency of the BPF regardless of process variations and environmental interferences. A pulse-width modulation (PWM) signal is used to regulate mechanical ultrasonic motion as described in further detail below.

The ultrasonic surgical system 300 for the ultrasonic surgical system includes a power source 310, an amplitude controller 320, and an automatic resonance tracking controller 360. The amplitude controller 320 includes a converter 330, a sensor 340 and a controller 350. The automatic resonance tracking controller 360 includes a non-resonant inverter 370, an ultrasonic transducer 380, and a comparator 390.

The power source 310 provides DC power to the converter 330 which modulates the amplitude of the DC power. The converter 330 may be a buck converter or a step-down converter. The sensor 340 then senses current passing to the automatic resonance tracking controller 360. The controller 350 receives the sensed results from the sensor 340 and generates a PWM control signal to control a duty cycle of the converter 330.

Figure 4:
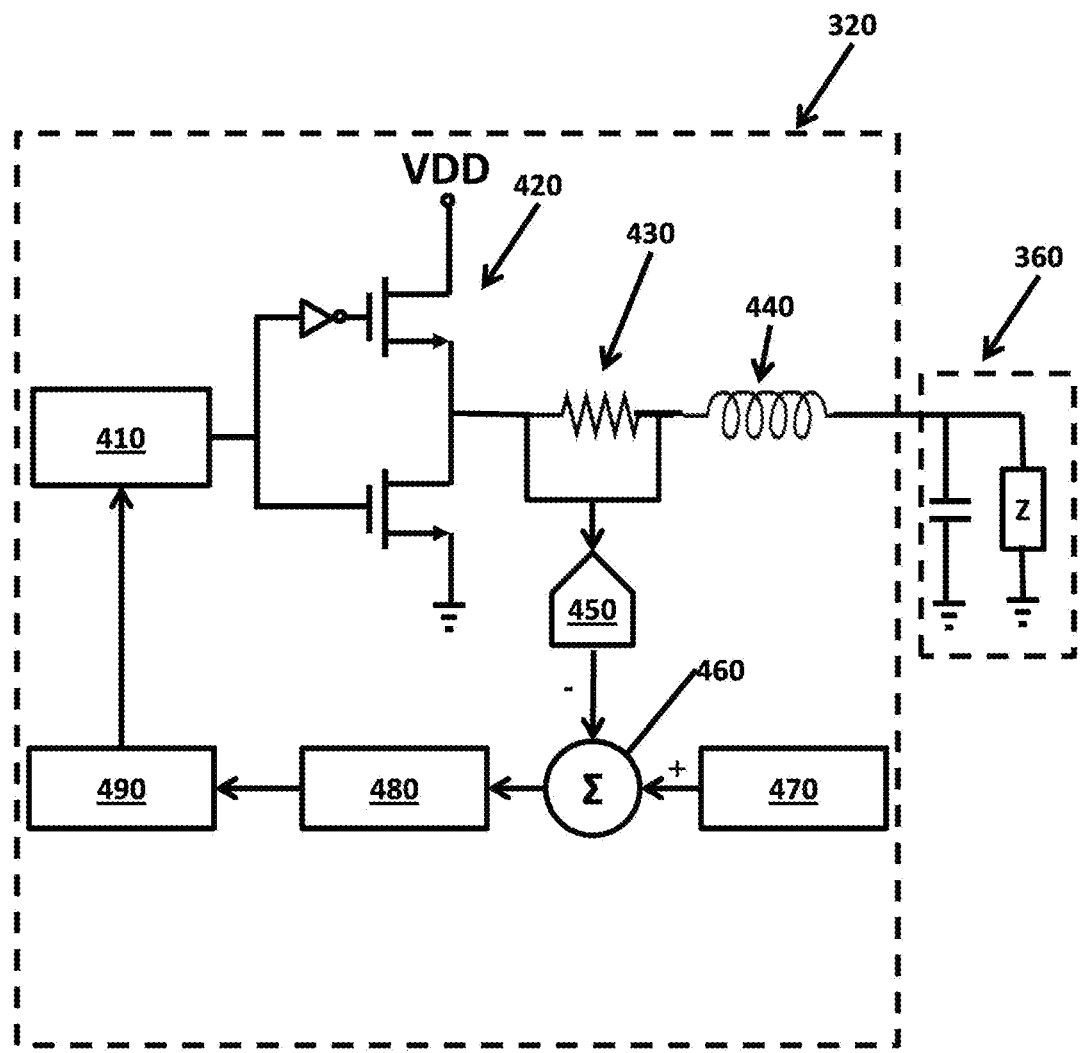
FIG. 4 is a circuit diagram illustrating an amplitude control circuit of the ultrasonic surgical system of FIG. 3 in accordance with embodiments of the present disclosure.

FIG. 4 shows a circuit diagram illustrating the amplitude controller 320 of FIG. 3. The amplitude controller 320 controls amplitudes of outputs of the converter 330 so that ultrasonic surgical system 300 generates mechanical ultrasonic motion suitable for treating tissue. The amplitude controller 320 includes a driver 410, a converter 420, a sensor 430, an analog to digital converter (ADC) 450, an adder 460, a reference provider 470, a controller 480, and a PWM generator 490. The automatic resonance tracking controller 360 is shown as a capacitor and a load in parallel, which is an electrical model at the resonant frequency of interest.

The driver 410 drives two field-effector transistors (FETs) of the converter 420 using PWM signals which have pulses with variable lengths at a regular interval. The widths of pulses turn on and off the FETs of the converter 420. The converter 420 receives power from a power source and outputs modulated power through the FETs. The output power flows through the sensor 430 in the form of DC. The sensor 430 includes a sensing resistor which drops voltage around the sensor resistor. The resistance value of the sensing resistor may be about 0.02 ohms (Ω). Since the DC passing through the sensing resistor also passes through the inductor 440, inductor current, $I_L$, passing through the inductor 440 may be determined by measuring the DC passing through the sensing resistor.

The sensed current by the sensor 430 is then sampled by the ADC 450. The size of bits of digital samples of the ADC 450 determines a level of accuracy of the measurements of the sensor 430. In embodiments, if the ADC 450 samples sensed data with 14 bits, the maximum range of the measured value can be divided up to 16,384 sub-ranges.

Generally, glitches or noise are inherently included in the samples of the ADC 450 because frequencies related to the glitches and noise are higher than the sampling frequency of the ADC 450. Averaging filters may be used to reduce the glitches and noises. In an aspect, the ADC 450 may include a zero-order sample and hold (ZOH).

In an aspect, the ADC 450 may include an adjuster and a compensator. Since the ADC 450 can only sample data whose magnitude is less than or equal to a predetermined maximum (e.g., 1 volt), the output data (e.g., current or voltage) of the converter 430 may be adjusted when the output data of the converter 430 is greater than the predetermined maximum. Thus, the adjuster adjusts the magnitude of the output data. After the ADC 450 samples the adjusted output, the compensator adjusts the output so that the compensated output has the same magnitude as the original data.

The adder 460 subtracts the sampled data (i.e., measured value of the DC) from a reference value provided by the reference provider 470. The adder 460 outputs a positive value when the reference value is greater than the sampled data, a negative value when the reference value is less than the measured value, and zero when the reference value is equal to the measured value.

In an aspect, the reference provider 470 may provide a different reference value. For example, the reference provider 470 may provide a reference value with a small load (e.g., 50 Ω) smaller than a reference value with a bigger load (e.g., 500 Ω). In this way, the amplitude controller 320 can appropriately control the amplitude of the DC in accordance with the load.

The controller 480 receives the output from the adder 460 and controls the duty cycle of the PWM signals. In embodiments, when the output from the adder 460 is positive, the controller 480 controls the PWM generator 490 to generate PWM signals with an increased duty cycle, and when the output from the adder 460 is negative, the controller 480 controls the PWM generator 490 to generate PWM signals with a decreased duty cycle. Duty cycle of PWM signals does not need to be changed when the output is zero. In an aspect, the adder 460 may subtract the reference value from the measured value. In this aspect, the signs of the output of the adder 460 are reversed from the above situation, and increase and decrease of the duty cycle are also reversed.

The PWM generator 490 generates PWM signals having an appropriate duty cycle in accordance with the controls of the controller 480. The generated PWM signals are used to drive the converter 420 by the driver 410. In this way, amplitude of the converter 420 is controlled to match the reference value output from the reference provider 470.

In embodiments, the controller 480 may be realized in digital domain and use a proportional-integral (PI) controller. Proportional gain $K_p$ and integral gain $K_i$ may be selected such that a high DC gain is achieved and static errors are reduced between the measured values and the reference value. The loop gain G(s) of the PI controller may be expressed in frequency domain as follows:

$$G(s) = K_p + \frac{K_i}{s}.$$

Due to the integral gain portion in the gain in the frequency domain, the PI controller introduces a zero to compensate for the pole, guaranteeing stability and DC gain to dampen the variations from the power supply.

Figure 5A:
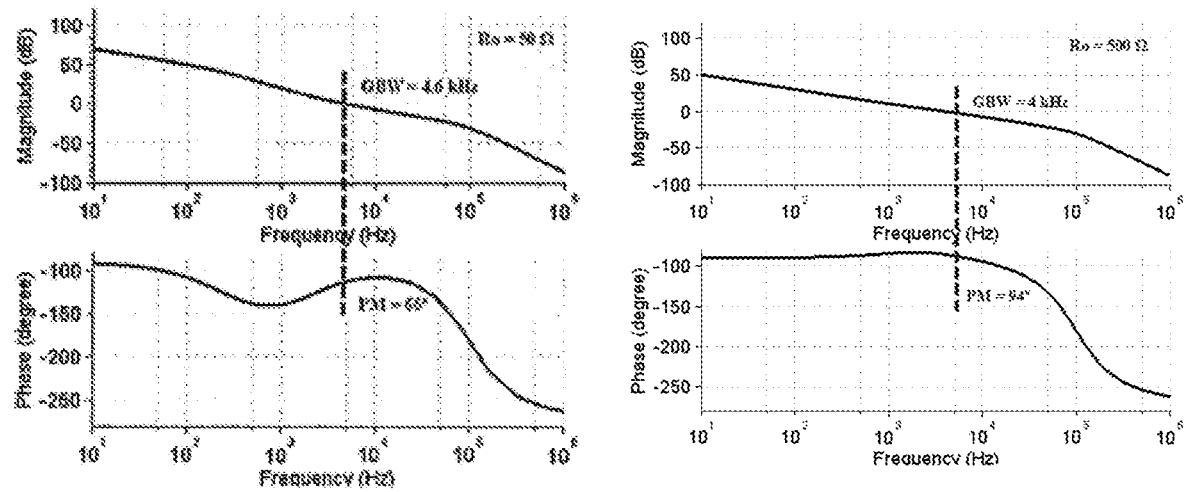
FIG. 5A is a graphical illustration of Bode plot of the amplitude control circuit of FIG. 4.

Graphical diagrams with a PI controller for two loads are illustrated in FIGS. 5A and 5 B. FIG. 5A shows Bode plots in the frequency domain. In embodiments, the proportional constant $K_p$ may be set to 16 and the integral gain $K_i$, may be set to 100,000 to ensure sufficient phase margin and avoid the high frequency poles due to the switching frequency which is set to 100 kHz. The Bode plot in the left is for the minimum 50 Ω load and the Bode plot in the right is for the maximum 500 Ω load. The top two graphs are Bode gain plots and the bottom two graphs are Bode phase plots. The horizontal axis for both Bode plots represents frequency in logarithmic scale. The vertical axis for the Bode gain plots represents magnitudes in decibel (dB) scale and that for the Bode phase plots represents phase.

As shown in FIG. 5A, when the load is 50 Ω and when the gain is 1 or the dB of the gain is zero, the gain bandwidth product (GBW) is 4.6 kHz which is less than one twentieth of the switching frequency, which is 5 kHz, but higher than 300 Hz, ensuring that a settling time is less than 18 milliseconds (ms). When the load is 500 Ω and when the dB of the gain is zero, the gain bandwidth product (GBW) is 4 kHz, which is within 5 kHz and 300 Hz, also ensuring that the settling time is less than 18 ms. Further, in both cases with the minimum and maximum loads, the system is stable with the PI controller.

Figure 5B:
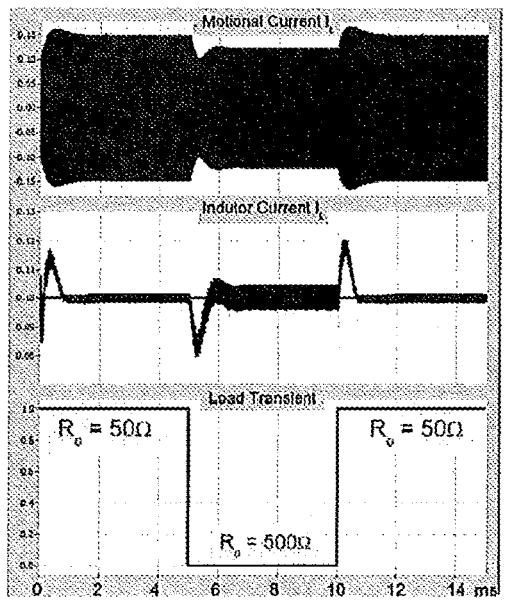
FIG. 5B is graphical illustration of plots of current amplitude controlled by the amplitude control circuit of FIG. 4.

FIG. 5B shows changes in amplitude of current according to changes in the load. The horizontal axis for all three graphs of FIG. 5B is time. The bottom graph shows that 50 Ω is loaded at the starting and the load is changed from 50Ω to 500 Ω at 5 ms and changed back to 50 Ω from 500 Ω at 10 ms. The middle graph shows changes in amplitude of current passing through the inductor, which may be the inductor 440 of FIG. 4. The amplitude controller 320 of FIG. 3 reacts and forces the inductor current to return to the reference value. Thus, changes in amplitude of current passing through inductor 440 occur when the load is loaded and changed. The top graph shows changes in amplitude of current passing through the ultrasonic transducer 380. The amplitude drops when a higher load is loaded. This is because the parasitic capacitor creates an offset in the motion current output even though the ultrasonic surgical system 300 forces more output voltage to the ultrasonic transducer 380. This drawback may be corrected by adjusting the reference value provided by the reference provider 470. In embodiments, if the ADC 450 uses 14 bits sample data and the reference provider 470 provides 5,000 as the reference value with 50 Ω load, the reference provider 470 may provide 7,000 as the reference value to the adder 460 with 500 Ω load to compensate the amplitude drop in the current passing through the automatic resonance tracking controller 360.

Figure 6A:
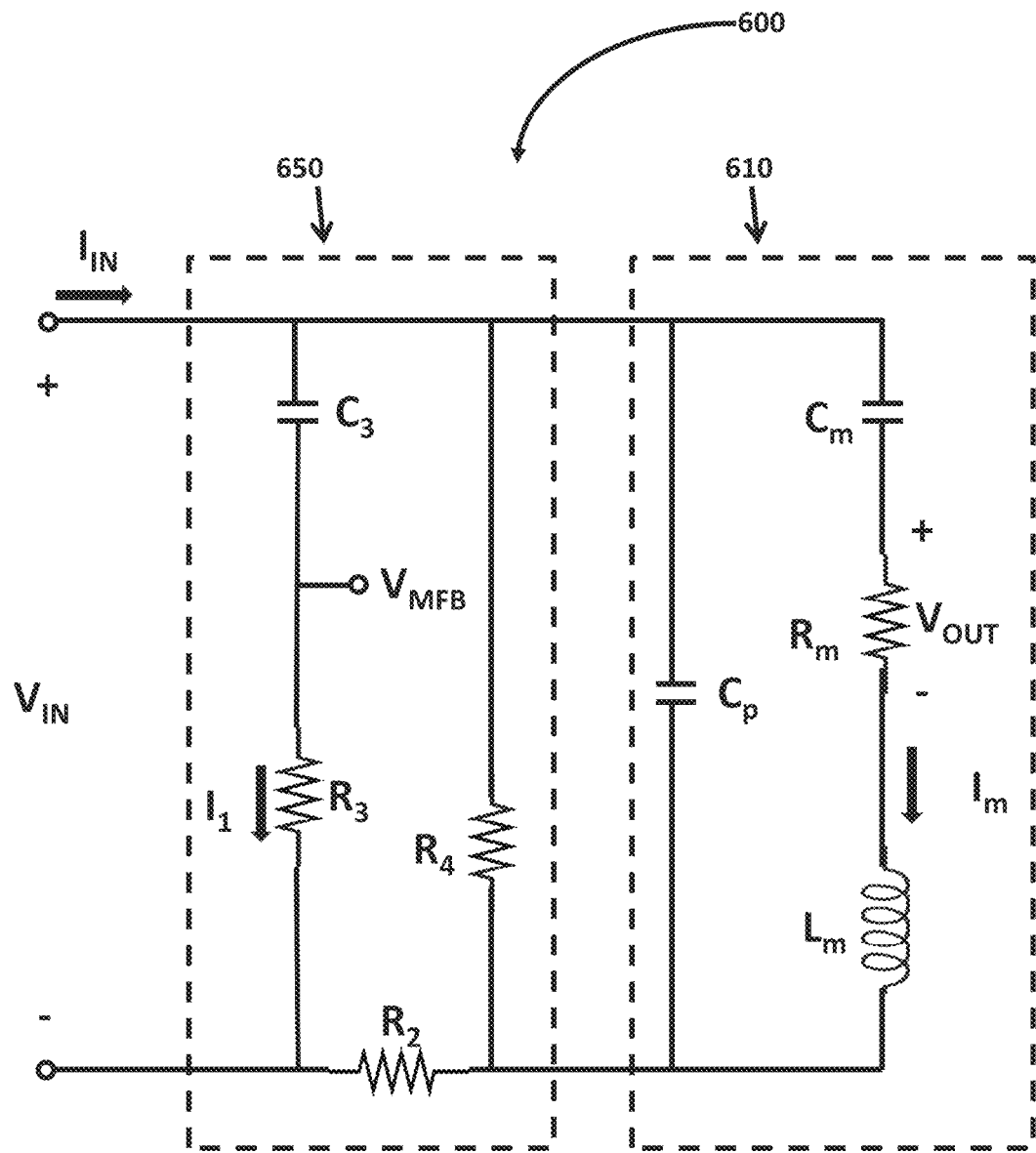
FIGS. 6A and 6B are electrical circuit diagrams illustrating an electrical circuit model of the ultrasonic transducer of FIG. 3 in accordance with embodiments of the present disclosure.

FIG. 6A shows a BPF oscillator model 600 illustrating automatic resonance tracking controller 360. The BPF oscillator model 600 includes a BPF circuit 610 and a motional sensing circuit 650. The BPF circuit 610, which represents an electrical model for an ultrasonic transducer 380, includes a motion capacitor having a capacitance value $C_m$, a motion resistor having a resistance value $R_m$, a motion inductor having an inductance value $L_m$, and a parasitic capacitor having a capacitance value $C_p$. The motion capacitor and the motion inductor represent mechanical motion of the ultrasonic transducer 380. That is mechanical ultrasonic motion are modeled as charging and discharging energy in the BPF circuit 610. At a resonance frequency of the BPF circuit 610, the motion resistor represents an end effector 190 of the ultrasonic surgical system 100 or a mechanical load. The resistance value $R_m$ may range from 50 Ω to 500 Ω. A capacitor and its capacitance value, an inductor and its inductance value, and a resistor and its resistance value may be used interchangeably hereinafter when there is no confusion, e.g., the motion resistor $R_m$ and the resistance value $R_m$ may be used interchangeably.

The impedance of the BPF circuit 610 may be calculated in the frequency domain. The parasitic capacitor is in parallel with the motion capacitor, the motion resistor, and the motion inductor. The impedance of the parasitic capacitor in the frequency domain $Z_{C_p}$ is as follows:

$$Z_{C_p} = \frac{1}{sC_p}.$$

In the frequency domain, the impedances of the motion capacitor $Z_{C_m}$, the impedance of the motion resistor $Z_{R_m}$, and the impedance of the motion inductor $Z_{L_m}$ are as follows:

$$Z_{C_m} = \frac{1}{sC_m},$$

$Z_{R_m} = R_m$, and $Z_{L_m} = sL_m$, respectively.

Since the motion capacitor, the motion resistor, and the motion inductor are connected in series, the total impedance of them in the frequency domain $Z_m$ is:

$$Z_m = \frac{1}{sC_m} + R_m + sL_m = \frac{L_m}{s}\left(s^2 + s\frac{R_m}{L_m} + \frac{1}{L_m C_m}\right).$$

Since the impedance $Z_m$ is in parallel with the parasitic capacitor, the total impedance $Z_{Total}$ of the BPF circuit 610 is:

$$Z_{Total} = \frac{1}{\frac{1}{Z_{C_p}} + \frac{1}{Z_m}} = \frac{Z_{C_p} Z_m}{Z_{C_p} + Z_m} =$$

$$\frac{1}{sC_p} \frac{\frac{L_m}{s}\left(s^2 + s\frac{R_m}{L_m} + \frac{1}{L_m C_m}\right)}{\frac{L_m}{s}\left(s^2 + s\frac{R_m}{L_m} + \frac{1}{L_m C_m}\right) + \frac{1}{sC_p}} = \frac{1}{sC_p} \frac{\left(s^2 + s\frac{R_m}{L_m} + \frac{1}{C_m L_m}\right)}{\left(s^2 + s\frac{R_m}{L_m} + \frac{C_m + C_p}{L_m C_m C_p}\right)}.$$

Here, the impedance of the BPF circuit 610 or the ultrasonic transducer 380 at resonance is $Z_{Total}$. In this BPF circuit 610, there are two resonant frequency, series resonant frequency $\omega_{0,series}$ and parallel resonant frequency $\omega_{0,parallel}$, which are expressed as:

$$\omega_{0,series} = \sqrt{\frac{1}{L_m C_m}} \text{ and}$$

$$\omega_{0,parallel} = \sqrt{\frac{C_m + C_p}{L_m C_m C_p}}.$$

However, only the series resonant frequency $\omega_{0,series}$ appears as the correct resonant frequency in mechanical ultrasonic motion of the ultrasonic transducer. The resonant frequency of the ultrasonic transducer 380 depends on the capacitance value $C_m$ of the motion capacitor and the inductance value $L_m$ of the motion inductor.

In order to measure motion current $I_m$ through the motion resistor, or through the ultrasonic transducer 380, the BPF oscillator model 600 includes the motional sensing circuit 650 which senses the motion current $I_m$. The motional sensing circuit 650 includes a capacitor having a capacitance value $C_3$ in series with a resistor having a resistance value $R_3$, which are in parallel with two resistors having resistance values $R_4$ and $R_2$. The resistance value $R_4$ is very large relative to the impedance of the BPF circuit 610 so that most of input current $I_{IN}$ goes through the BPF circuit 610. In other words, the resistor $R_4$ looks like an open circuit. Thus, the BPF oscillator model 600 can be simplified as FIG. 5B by ignoring the resistor $R_4$ and simplifying the BPF circuit 610 as a parallel combination of the parasitic capacitor $C_p$ and an impedance block Z representing the other passive components, $L_m$, $R_m$, and $C_m$.

The motional sensing voltage $V_{MFB}$ is related to the motion current $I_m$. The relationship between the motional sensing voltage $V_{MFB}$ and the motion current $I_m$ is:

$$V_{MFB} = I_1 R_3 - I_2 R_2 = K \cdot I_m.$$

Thus, this relationship indicates that the motional sensing voltage $V_{MFB}$ is proportional to the motion current $I_m$ by a gain of K. The gain K can be expressed in the frequency domain as follows:

$$K = \frac{\left[Z\left(R_3 - \frac{C_p R_2}{C_3}\right)\right] - \frac{R_2}{sC_3}}{\frac{1}{sC_3} + R_3}.$$

The relationship between the motional sensing voltage $V_{MFB}$ and the motion current $I_m$ also shows that the motional sensing circuit 650 directly measures the motion current $I_m$. However, this motional sensing circuit 650 is frequency-dependent and a function of the load Z. Selection of passive components $R_2$, $R_3$, and $C_3$ may be based on the variations in Z, different loading conditions, and parasitic parallel capacitor $C_p$ over a wide range of frequencies. $R_3$ may be matched to $$\frac{C_p R_2}{C_3}$$

to make the motional sensing circuit 650 a load independent circuit and to completely cancel its effect on the measured signal, as can be observed in the numerator of the equation of the gain K. This selection is clearly load independent and may make the sensing signal more robust against variations of the load, ensuring good tracking over wide load transients.

With reference to FIG. 3, the non-resonant inverter 370 receives the modulated DC power from the converter 330 and inverts to AC power having the resonant frequency of the ultrasonic transducer 380. The non-resonant inverter 370 is driven by output signals from the comparator 390. The non-resonant inverter 370 may include any suitable topology such as an H-bridge (e.g., full bridge), a half bridge, and the like.

In an aspect, the output signals from the comparator 390 may be digitally generated by the controller 350. In this embodiment, the controller 350 not only generates DPWM signals to drive the converter 330 but also generates resonant signals, which have 50 percent duty cycle, for the non-resonant inverter 370. Nevertheless, the controller 350 may not control the automatic resonance tracking controller 360. The controller 350 just receives outputs from the comparator 390, generates resonant signals according to the outputs of the comparator 390, and provides the generated resonant signals to the non-resonant inverter 370.

In an aspect, the controller 350 may be realized using a programmable gate array (PGA), field-programmable gate array (FPGA), application-specific integrated circuit (ASIC), or complex programmable logic device (CPLD). This list provides examples and may further include other techniques and devices as those having ordinary skill in the art would appreciate.

The non-resonant inverter 370 inverts the DC power to the AC signal, whose frequency is independent of the switching frequency of the non-resonant inverter 370, by tracking the resonant frequency of the ultrasonic transducer 380.

In an aspect, a transformer may be electrically coupled between the non-resonant inverter 370 and the ultrasonic transducer 380 so that the transformer may increase or decrease the amplitude of the inverted AC power.

The ultrasonic transducer 380 received the AC power having a first frequency and generates mechanical ultrasonic motion. When the first frequency does not match the resonant frequency of the ultrasonic transducer 380, the comparator 390 receives the motion current $I_m$, as described in FIGS. 6A and 6B, and automatically tracks the resonant frequency of the ultrasonic transducer 380.

Specifically, the motion current $I_m$ passing through the ultrasonic transducer 380 fluctuates based on deviations of the first frequency from its resonant frequency. In other words, when the first frequency does not match the resonant frequency, the motion current $I_m$ goes up or down from zero. Thus, the motion current $I_m$ has information of the resonant frequency of the ultrasonic transducer 380.

Figure 7:
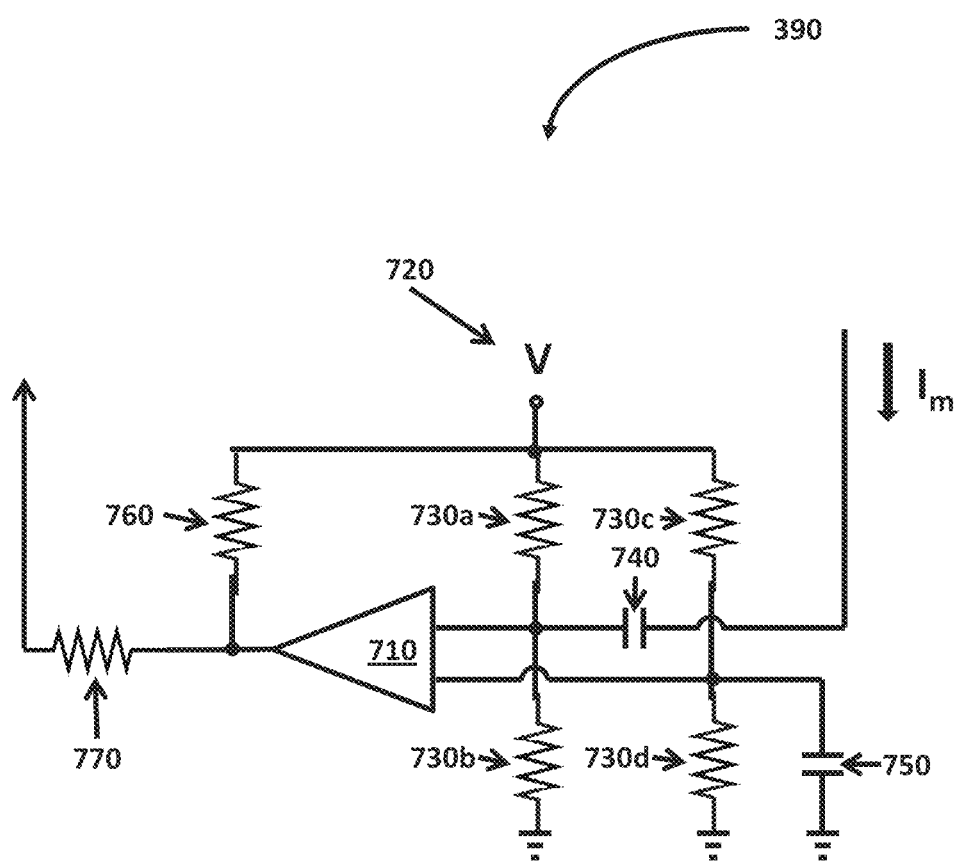
FIG. 7 is a circuit diagram of a comparator of the ultrasonic transducer of FIG. 3 in accordance with embodiments of the present disclosure.

The comparator 390 amplifies the motion current $I_m$ to generate output signals having the resonant frequency information of the ultrasonic transducer 380. As an example, FIG. 7 shows a circuit diagram of the comparator 390 of FIG. 3. The comparator 390 includes an amplifier 710 which has first and second input ports and an output port. Each of the two input ports provides a voltage to the amplifier 710 which subtracts one voltage from the other and amplifies the difference.

A voltage source 720 provides a voltage to the amplifier 710 via the first and the second input ports. The comparator 390 includes four resistors 730*a-d*. The first pair of resistors 730*a* and 730*b* are connected in series and the second pair of resistors 730*c* and 730*d* are connected in series, while the first pair of resistors and the second pair of resistors are connected in parallel. The voltage source 720 is connected to the resistors 730*a* and 730*c*, and the resistors 730*b* and 730*d* are connected to the ground. The first input port is connected to the connection point between the two resistors 730*a* and 730*b*, and the second input port is connected to the connection point between the two resistors 730*c* and 730*d*.

In this example, the resistance values of the four resistors 730*a*-730*d* are same to each other. Thus, when there is no input from an external circuit, the first input port and the second input port are provided with the same voltage, which is the half of the voltage that the voltage source 720 provides, according to the voltage divider rule. Thus, the output of the amplifier, or the output of the comparator 390 is a zero AC motional signal current. Specifically, during an idle condition, a static output will turn-on half side of the non-resonant inverter 370, resulting in constant DC output. Thus, no power is delivered to the load.

The connection point between the resistors 730*a* and 730*b* is also connected to a capacitor 740 which receives the motion current $I_m$ from the ultrasonic transducer 380 and the second input port is also connected to a capacitor 750 which is connected to the ground. The capacitor 740 prevents DC component of the motion current $I_m$ from being provided to the amplifier 710. Now, when the motion current $I_m$ fluctuates, the input to the first input port also fluctuates accordingly and the amplifier 710 amplifies the difference between inputs from the first and second input ports due to the fluctuations. In this way, the resonant frequency information included in the motion current $I_m$ is amplified to and included in the outputs of the comparator 390.

The comparator 390 further includes a feedback resistor 760 which is connected between the voltage source 720 and the output port of the amplifier 710, and another resistor 770 which is connected to the output port of the amplifier 710. In order to limit the current flowing into the controller 350, the resistor 770 having a high resistance value (e.g., 1 kΩ) may be placed between the comparator 390 and the controller 350.

In embodiments, the amplifier 710 may have an infinite gain so that an analog signal (i.e., motion current $I_m$) may be converted to a digital signal that can directly drive the non-resonant inverter 370. Then, the non-resonant inverter 370 generates AC having the resonant frequency of the ultrasonic transducer 380 which then turns to generate mechanical ultrasonic motion having the resonant frequency of the ultrasonic transducer 380. In reality, however, the comparator 390 has a limited but very high gain, which may be higher than the resistance value $R_m$ of the motion resistor, as described in FIG. 6A, or mechanical resistance, and outputs a signal similar to the digital signal. The controller 350 then receives this signal and generates a DPWM signal having the resonant frequency information to drive the non-resonant inverter 370.

Figure 8:
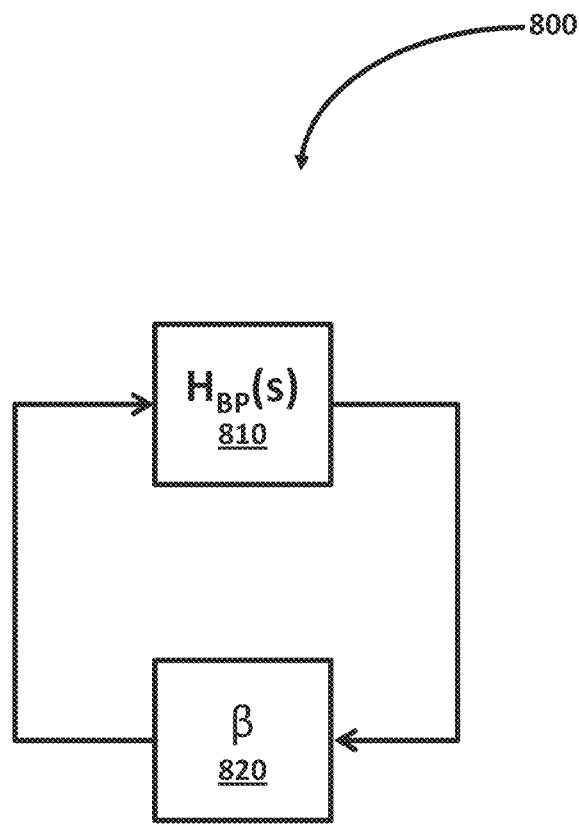
FIG. 8 is a block diagram illustrating a closed loop control model of the ultrasonic transducer of FIG. 3 in accordance with embodiments of the present disclosure.

FIG. 8 shows a block diagram illustrating a closed loop feedback system 800 of the ultrasonic transducer 380 and the comparator 390 of FIG. 3. In the closed loop feedback system 800, a BPF 810 represents the ultrasonic transducer 380 and a voltage limiter 820 represents the comparator 390 of FIG. 3. Here, the BPF 810 and the voltage limiter 820 forms the closed loop feedback system 800 as the ultrasonic transducer 380 and the comparator 390 form a closed loop feedback system. In order to have stable oscillations in the closed loop feedback system 800, the following criteria should be met:

$|\beta \cdot A| = 1$ and $\angle \beta \cdot A = 2n\pi$, where $\beta$ is the gain of the voltage limiter 820, A is a BPF transfer function, $H_{BP}(S)$, and n is an integer greater than or equal to zero. The above criteria are called Barkhausen stability criterion.

The BPF transfer function $H_{BP}(s)$ is expressed as follows:

$$H_{BP}(s) = \frac{sK_1}{s^2 + s\frac{\omega_0}{Q} + \omega_0^2},$$

where $K_1$ is the numerator coefficient of the BPF 810, $\omega_0$ is the center frequency of the BPF 810, and Q is the quality factor of the BPF 810. Then, the transfer function $H_{CL}(s)$ of the closed loop feedback system 800 is:

$$H_{CL}(s) = \frac{H_{BP}(s)}{1 - \beta \cdot H_{BP}(s)} =$$

$$\frac{H_{BP}(s)}{1 - LG(s)} = \frac{\frac{sK_1}{s^2 + s\frac{\omega_0}{Q} + \omega_0^2}}{1 - \frac{s\beta \cdot K_1}{s^2 + s\frac{\omega_0}{Q} + \omega_0^2}} = \frac{sK_1}{s^2 - s\left(\beta \cdot K_1 - \frac{\omega_0}{Q}\right) + \omega_0^2},$$

where $\beta$ is the gain of the voltage limiter 820 and LG(s) is the loop gain of the closed loop system 800.

Based on the Barkhausen stability criterion, the loop gain LG(s) has to be one to make the denominator of the transfer function $H_{CL}(s)$ of the closed loop feedback system zero, which makes the magnitude of the closed loop feedback system 800 infinite and ensures oscillations. Practically, the ultrasonic transducer suffers from environmental variations such as load or temperature changes which may result in shifts of resonant frequency. However, the oscillating center frequency locates exactly at the resonant frequency, which guarantees that the closed loop feedback system 800 automatically tracks the resonant frequency of the ultrasonic transducer. The complexity of this feature is as simple as ordinary second order system as shown in the denominator of the transfer function $H_{CL}(s)$.

Figure 6B:
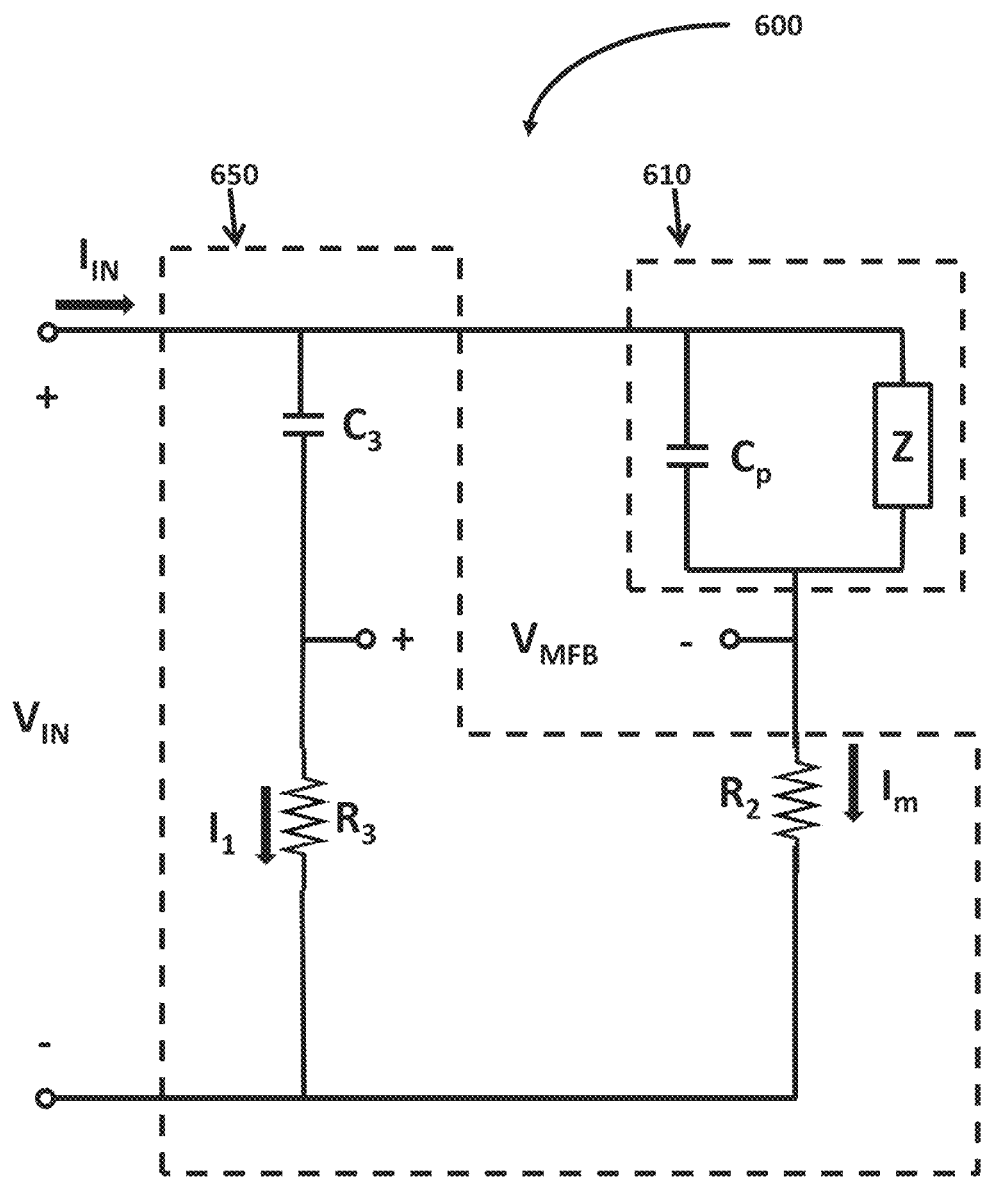

In an aspect, the gain $\beta$ of the voltage limiter 820 has to be greater than a minimum value of $$\frac{\omega_0}{K_1 \cdot Q}$$

that represents the peak magnitude value of the BPF 810 at the resonant frequency, to meet the Barkhausen stability criterion for sustained oscillation, and has to be greater than the resistance value $R_m$ of the motion resistor based on the description of FIGS. 6A and 6B. If the gain $\beta$ is smaller than $$\frac{\omega_0}{K_1 \cdot Q},$$

the output signal amplitude will be insufficient to sustain the oscillations and will eventually settle down to a static state.

Since other modifications and changes may be made to fit particular operating requirements and environments, it is to be understood by one skilled in the art that the present disclosure is not limited to the illustrative examples described herein and may cover various other changes and modifications which do not depart from the spirit or scope of this disclosure.

What is claimed is:

1. An ultrasonic motion generator comprising:
a non-resonant inverter configured to invert direct current (DC) to alternating current (AC) having a first frequency;
an ultrasonic transducer configured to generate an ultrasonic motion based on the AC;
a motional sensing circuit electrically coupled with the ultrasonic transducer in parallel, the motional sensing circuit including a capacitor, a first resistor in series with the capacitor, and a second resistor in parallel with the capacitor and the first resistor and in series with the ultrasonic transducer, wherein the motional sensing circuit is configured to sense a motion current passing though the ultrasonic transducer; and
a comparator configured to automatically detect a deviation of the first frequency from a resonant frequency of the ultrasonic transducer based on the motion current and to generate an output signal based on the deviation to drive the non-resonant inverter.

2. The ultrasonic motion generator according to claim 1, wherein the motion current is a current passing through the second resistor.

3. The ultrasonic motion generator according to claim 1, wherein, in a frequency domain, a magnitude of a product of a gain of the comparator and a gain of the ultrasonic transducer is equal to one.

4. The ultrasonic motion generator according to claim 3, wherein, in the frequency domain, a phase of the product of the gain of the comparator and the gain of the ultrasonic transducer is equal to an integer multiple of two Pi radians.

5. The ultrasonic motion generator according to claim 1, wherein the comparator has a high open loop gain.

6. The ultrasonic motion generator according to claim 1, further comprising a transformer electrically coupled with the non-resonant inverter and the ultrasonic transducer, and configured to control an amplitude of the AC inverted by the non-resonant inverter.

7. The ultrasonic motion generator according to claim 1, wherein a longitudinal displacement of the ultrasonic motion is based on amplitude of the AC inverted by the non-resonant inverter.

8. The ultrasonic motion generator according to claim 1, wherein the non-resonant inverter is controlled by a digital resonant signal based on the output signal of the comparator.

9. An ultrasonic surgical apparatus for treating tissue, comprising:

a power source configured to output direct current (DC);
an ultrasonic motion generator electrically coupled with the power source, the ultrasonic motion generator including:
  a non-resonant inverter configured to invert the DC to alternating current (AC) having a first frequency;
  an ultrasonic transducer configured to generate an ultrasonic motion based on the AC;
  a motional sensing circuit electrically coupled with the ultrasonic transducer in parallel, the motional sensing circuit including a capacitor, a first resistor in series with the capacitor, and a second resistor in parallel with the capacitor and the first resistor and in series with the ultrasonic transducer, wherein the motional sensing circuit is further configured to sense a motion current passing though the ultrasonic transducer; and
  a comparator configured to automatically detect a deviation of the first frequency from a resonant frequency of the ultrasonic transducer based on the motion current and to generate an output signal based on the deviation to drive the non-resonant inverter; and
a controller coupled with the motional sensing circuit and the comparator, and configured to control an amplitude of the DC.

10. The ultrasonic surgical apparatus according to claim 9, wherein the motion current is a current passing through the second resistor.

11. The ultrasonic surgical apparatus according to claim 9, wherein, in a frequency domain, a magnitude of a product of a gain of the comparator and a gain of the ultrasonic transducer is equal to one.

12. The ultrasonic surgical apparatus according to claim 11, wherein, in the frequency domain, a phase of the product of the gain of the comparator and the gain of the ultrasonic transducer is equal to an integer multiple of two Pi radians.

13. The ultrasonic surgical apparatus according to claim 9, wherein the comparator has a high open loop gain.

14. The ultrasonic surgical apparatus according to claim 9, wherein the power source includes:
  a power supply configured to generate DC power; and
  a converter configured to modulate the DC power.

15. The ultrasonic surgical apparatus according to claim 14, wherein the controller is further configured to generate a digital pulse-width modulation signal based on the motion current to drive the converter.

16. The ultrasonic surgical apparatus according to claim 14, wherein a longitudinal displacement of the ultrasonic motion is based on amplitude of the DC converted by the converter.

17. The ultrasonic surgical apparatus according to claim 9, wherein the controller is further configured to generate a digital pulse-width modulation signal based on the output signal to drive the non-resonant inverter.

18. The ultrasonic surgical apparatus according to claim 9, wherein the ultrasonic motion generator further includes a transformer electrically coupled with the non-resonant inverter and the ultrasonic transducer and configured to control amplitude of the AC inverted by the non-resonant inverter.

19. An ultrasonic system for treating tissue, comprising:
a ultrasonic surgical apparatus including:
  a power source configured to provide direct current (DC);
  an ultrasonic motion generator electrically coupled with the power source, the ultrasonic motion generator including:
    a non-resonant inverter configured to invert direct current (DC) to alternating current (AC) having a first frequency;
    an ultrasonic transducer configured to generate an ultrasonic motion based on the AC;
    a motional sensing circuit electrically coupled with the ultrasonic transducer in parallel, the motional sensing circuit including a capacitor, a first resistor in series with the capacitor, and a second resistor in parallel with the capacitor and the first resistor and in series with the ultrasonic transducer, wherein the motional sensing circuit is configured to sense a motion current passing though the ultrasonic transducer; and
    a comparator configured to automatically detect a deviation of the first frequency from a resonant frequency of the ultrasonic transducer based on the motion current and to generate an output signal based on the deviation to drive the non-resonant inverter;
  a sensor configured to sense the DC passing from the power source to the ultrasonic motion generator; and
  a controller coupled to the sensor and the comparator, and configured to control an amplitude of the DC; and
an end effector configured to apply the generated ultrasonic motion to tissue for treating the tissue.

* * * * *